United States Patent
Bell

(10) Patent No.: US 10,524,510 B2
(45) Date of Patent: Jan. 7, 2020

(54) HEATER FOR A VAPORIZATION DEVICE

(71) Applicant: Funai Electric Company, Ltd., Osaka (JP)

(72) Inventor: Byron V. Bell, Lexington, KY (US)

(73) Assignee: FUNAI ELECTRIC CO., LTD. (JP)

( * ) Notice: Subject to any disclaimer, the term of this patent is extended or adjusted under 35 U.S.C. 154(b) by 0 days.

(21) Appl. No.: 15/643,552

(22) Filed: Jul. 7, 2017

(65) Prior Publication Data

US 2019/0008205 A1    Jan. 10, 2019

(51) Int. Cl.
| A24F 13/00 | (2006.01) |
| A24F 47/00 | (2006.01) |
| H05B 3/34 | (2006.01) |
| F22B 1/28 | (2006.01) |
| H05B 3/22 | (2006.01) |

(52) U.S. Cl.
CPC ............ *A24F 47/008* (2013.01); *F22B 1/284* (2013.01); *H05B 3/22* (2013.01); *H05B 3/34* (2013.01); *H05B 2203/014* (2013.01); *H05B 2203/021* (2013.01)

(58) Field of Classification Search
CPC .................................................... A24F 37/008
USPC .................................................. 131/329, 328
See application file for complete search history.

(56) References Cited

U.S. PATENT DOCUMENTS

| 9,449,797 | B2 | 9/2016 | Singh et al. | |
| 10,123,568 | B1* | 11/2018 | Zhu ........................ | A24F 47/008 |
| 2004/0047645 | A1 | 3/2004 | No et al. | |
| 2008/0048054 | A1 | 2/2008 | Peters et al. | |
| 2009/0220222 | A1 | 9/2009 | Rabin et al. | |
| 2011/0210458 | A1 | 9/2011 | Brodbeck et al. | |
| 2014/0208838 | A1 | 7/2014 | Moon et al. | |
| 2015/0217068 | A1* | 8/2015 | Wakalopulos ........ | A61M 15/06 128/202.21 |
| 2016/0021934 | A1* | 1/2016 | Cadieux ............... | A24F 47/008 131/328 |
| 2017/0027225 | A1 | 2/2017 | Buchberger et al. | |
| 2017/0055582 | A1 | 3/2017 | Blandino et al. | |
| 2017/0105452 | A1 | 4/2017 | Mironov et al. | |
| 2017/0208864 | A1* | 7/2017 | Anderson, Jr. ....... | A61M 15/06 |
| 2017/0265526 | A1 | 9/2017 | Li et al. | |
| 2018/0104214 | A1* | 4/2018 | Raichman .............. | A61P 25/36 |

FOREIGN PATENT DOCUMENTS

| CN | 104126876 A | 11/2014 |
| CN | 105901775 A | 8/2016 |

OTHER PUBLICATIONS

Brooks, D.; Selvy, A, "A high dielectric constant lets these heating modules be compact and heat up quickly," Basics of Ceramic Heaters, Aug. 28, 2013, pp. 1-3.
"Evaporation Boats," Midwest Tungsten Service, Web Page, pp. 1-7, Aug. 11, 2016.

* cited by examiner

*Primary Examiner* — Phuong K Dinh
(74) *Attorney, Agent, or Firm* — Luedeka Neely Group, PC

(57) ABSTRACT

A heater for a vaporization device includes a fluid reservoir and a porous and permeable heating element made of an electrically conductive material and located within the reservoir. The reservoir and the heating element located within the reservoir define a fluid volume sufficient to capture and retain a fixed volume of fluid ejected from an ejection head in the vaporization device. Application of electrical energy to the heating element vaporizes the fixed volume of fluid in a fixed amount of time.

12 Claims, 3 Drawing Sheets

HEATER FOR A VAPORIZATION DEVICE

TECHNICAL FIELD

One of the applications of a fluidic ejection device is to jet a solution on to another device where a secondary function may be performed. A common secondary function is to vaporize a solution using a heater such that the contents of the solution can be vaporized so as to deliver the solution as a gaseous substance. Applications of such technology include, but are not limited to, metering and vaporization devices for electronic cigarettes, vapor therapy, gaseous pharmaceutical delivery, vapor phase reactions for micro-labs, and the like. A problem associated with such devices is efficient vaporization of the fluid. This document discloses improved heaters and methods for improving the vaporization efficiency of heaters for vaporization devices.

BACKGROUND AND SUMMARY

When vaporizing a fluid it is highly desirable for 100% of the fluid to vaporize so that liquid is not discharged from the vaporization device. Conventional heaters desire improvement in that invariably some liquid is discharged from the vaporization device or otherwise remains within the vaporization device. In the case of fluid that remains in the vaporization device, such liquid may be exposed to excessively high temperatures which causes undesirable smoking or undesirable chemical reactions of the liquid due to exposure to the high temperatures.

Rapid heating of the heater is also essential to assuring that all of the liquid conveyed to the heater is vaporized. Complete vaporization of the fluid is important in order to avoid entraining liquid droplets in the vapor stream from the vaporization device. In some applications, the discharge of liquid is not only undesirable, but may be detrimental to the user. In order to avoid the discharge of liquid droplets from a vaporization device, the stream of fluid ejected to the heater must be efficiently captured by the heater, and completely vaporized at approximately the same rate as the fluid arrives to the heater.

In view of the foregoing, embodiments of the disclosure provide a heater configuration that advantageously avoids problems associated with conventional heaters and effectively contains the jetted fluid and vaporizes all of the contained fluid within a desired amount of time and at desired temperature levels.

In one aspect, the invention provides a heater for a vaporization device including a fluid reservoir and a porous and permeable heating element made of an electrically conductive material and located within the reservoir. The reservoir and the heating element define a fluid volume sufficient to capture and retain a fixed volume of fluid ejected from an ejection head in the vaporization device. Application of electrical energy to the heating element vaporizes the fixed volume of fluid in a fixed amount of time.

In some embodiments, the fluid reservoir is made of a material that is not electrically conductive, such as ceramic.

In another embodiment, the heating element is a mesh.

In yet another embodiment, the heating element is made of interwoven wire, and made of kanthal or nichrome or stainless steel or combinations thereof.

BRIEF DESCRIPTION OF THE DRAWINGS

Other features and advantages of disclosed embodiments may be evident by reference to the following detailed description, drawings and claims wherein:

DETAILED DESCRIPTION OF EMBODIMENTS

Figure 1:
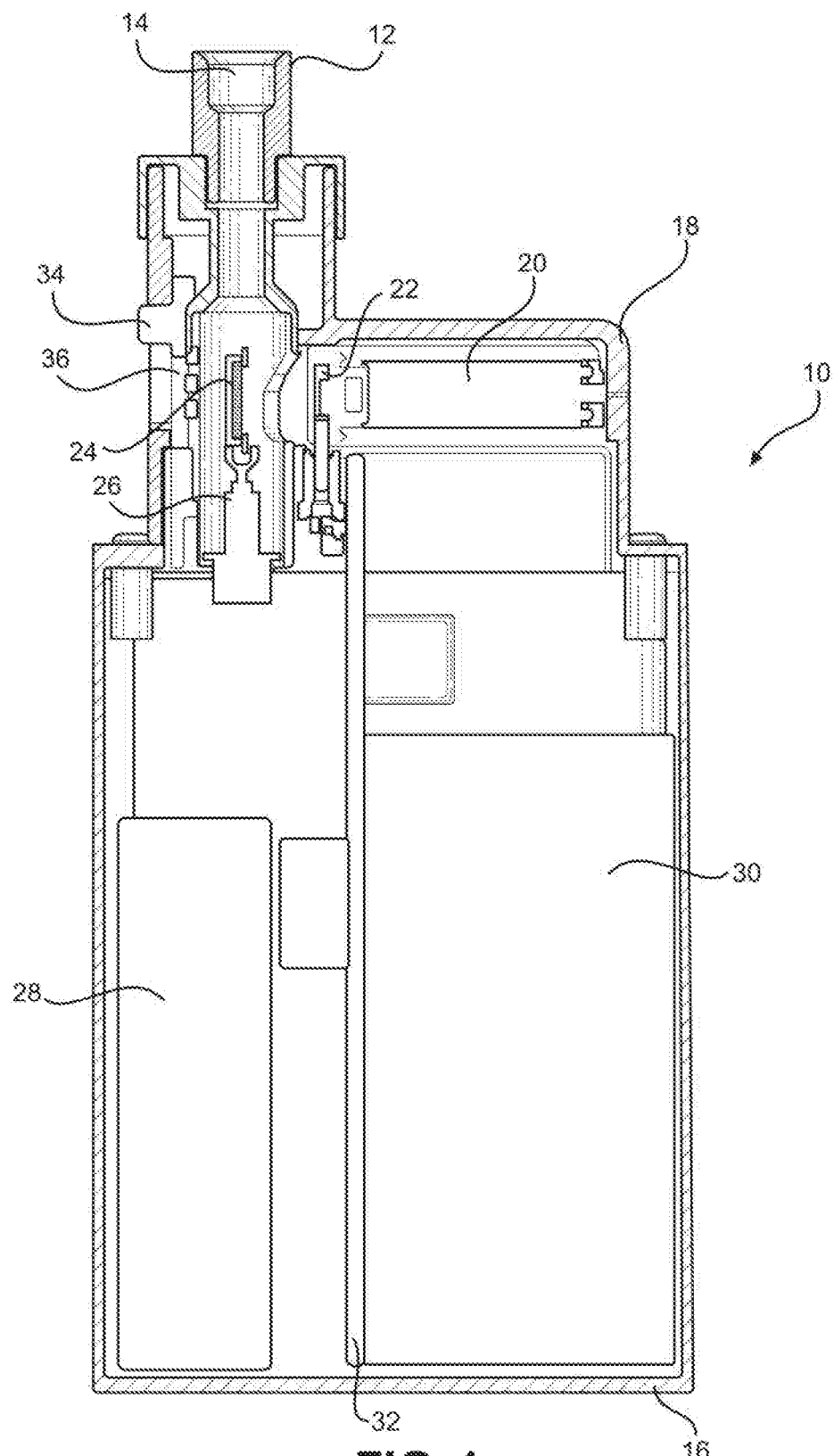
FIG. 1 is a cross-sectional view, not to scale, of a vaporization device according to an embodiment of the disclosure.
Figure 2:
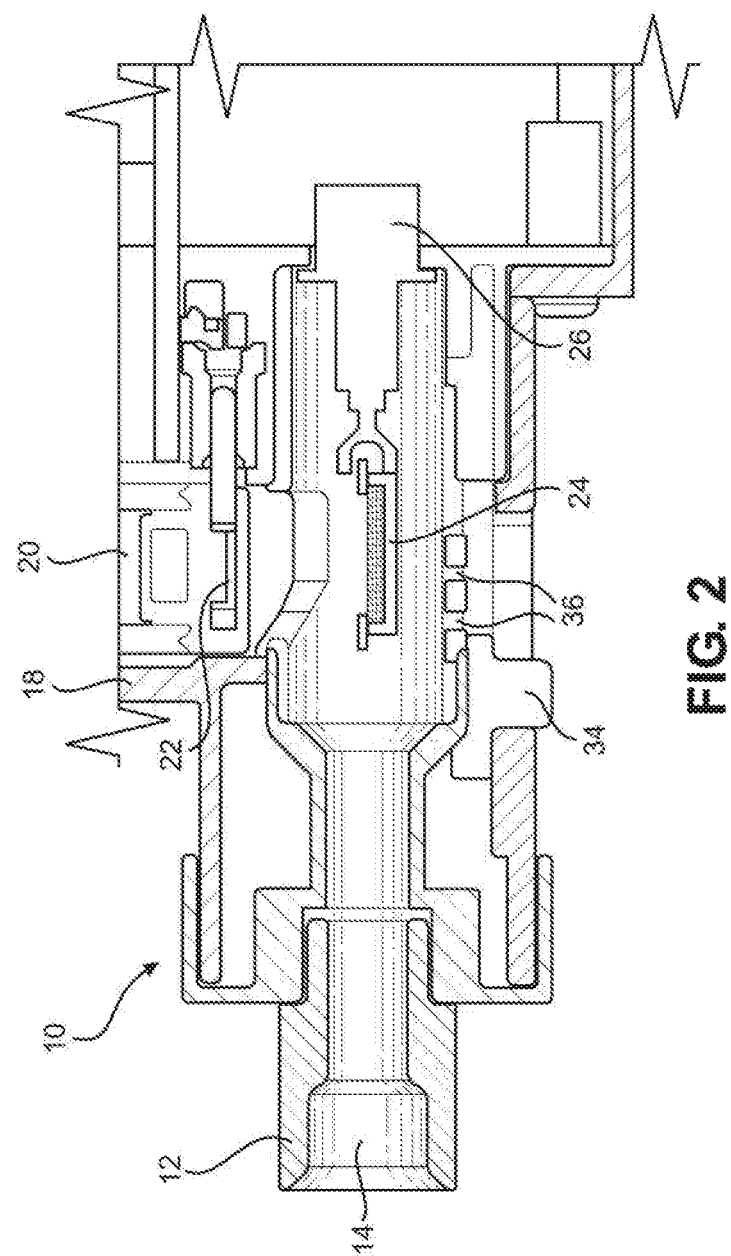
FIG. 2 is a close-up view, not to scale, of a portion of the vaporization device of FIG. 1.
Figure 3:
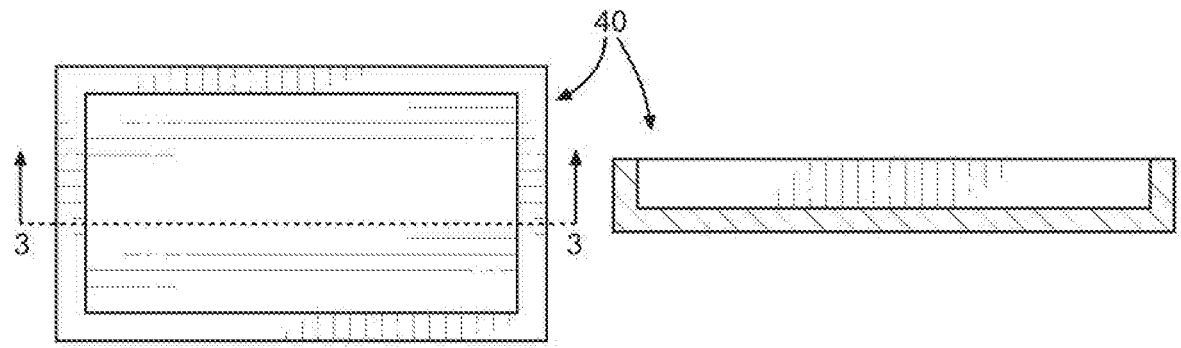
FIG. 3 is a two-dimensional view, not to scale, of a heater base according to the disclosure.
Figure 4:
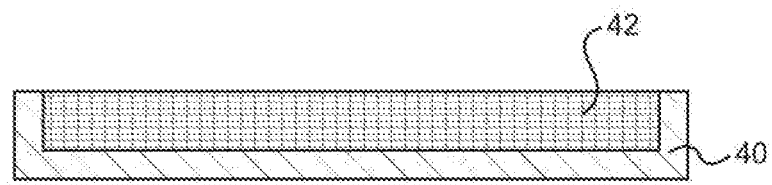
FIG. 4 is a cross-sectional view of the heater base of FIG. 3 with a heating element located therein to provide a heater according to the disclosure.
Figure 5:
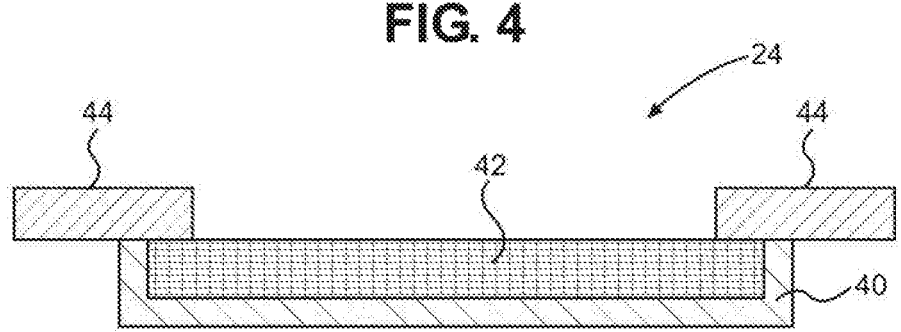
FIG. 5 shows the heater of FIG. 4 with electrodes provided thereon.

The disclosure is directed to a vaporization device 10 as shown in FIGS. 1 and 2 and heater therefor as shown in FIGS. 3-6. Such devices 10 may be used for a wide variety of applications wherein a liquid is ejected onto a heater to provide a vapor stream as described in more detail below. Such devices 10 are typically hand held devices such as electronic cigarettes that have a mouthpiece 12 for inhaling vapors generated by the device 10. The mouthpiece 12 includes a conduit 14 for flow of vapors out of the device 10. The main components of the device 10 include a housing body 16, a removable cartridge cover 18, a removable fluid supply cartridge 20, an ejection head 22 associated with the fluid supply cartridge 20, and a heater 24 for vaporizing fluid ejected from the ejection head 22 and a holder 26 providing electrical connections for the heating element 24. Other components associated with the vaporization device 10 include a rechargeable power supply 28, a main circuit board 30, and a vaporization driver card 32. An enlarged portion of the vaporization device is shown in FIG. 2.

The mouthpiece 12, as well as the body 16 of the vaporization device 10 may be made from a wide variety of materials including plastics, metals, glass, ceramic and the like provided the materials are compatible with the fluids to be ejected and vaporized by the device 10. A particularly suitable material may be selected from polyvinyl chloride, high density polyethylene, polycarbonate, stainless steel, surgical steel, nickel-plated steel, and the like. All parts, including the mouthpiece 12, and body 16 that come in contact with fluids and vapors may be made of plastic. The conduit 14 may be made of metal such as stainless steel or other material that is resistant to heat and vapors generated by the device.

As shown in FIG. 1, the housing body 16 may include the circuit board 30 and the driver card 32 for providing the logic circuitry for the heater 24 (described in more detail below) and ejection head 22. The rechargeable battery 28 may also be housed in the housing body 16. In another embodiment, a removable, non-rechargeable battery may be housed in the housing body. Electrical contacts, such as a USB (not shown) may be used to recharge the battery 28 and to change program setting for the ejection head 22 and heater 24. The microfluidic ejection head 22 is in fluid flow communication with the fluid supply cartridge 20 that provides fluid to be ejected by the ejection head 22.

An inlet air flow control device may be included to provide backpressure control on the ejection head 22. The inlet air flow control device may include a damper slide 34 and air inlet holes 36 that allow air to be drawn into the conduit 14 adjacent the heater 24 and ejection head 22 so that excessive negative pressure on the ejection head 22 can be avoided.

An important component of the vaporization device 10 is the heater 24, shown in greater detail in FIGS. 3-6. The heater 24 includes a fluid reservoir 40 and an electrically conductive porous and permeable heating element 42 located within the reservoir 40. Electrodes 44 connect to the heating element 42.

Figure 6:
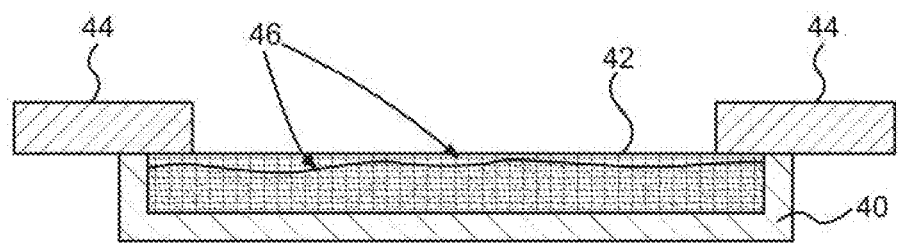
FIG. 6 depicts loading of a fluid to be vaporized into the heater of FIG. 5

The reservoir 40 is made of a fluid impermeable insulative material, preferably ceramic. The reservoir 40 is configured to provide a reservoir of appropriate volume to contain both a desired amount of fluid 46 to be vaporized, and the heating element 42 (FIG. 6). The reservoir 40 is desirably configured for a fluid volume of from about 10 to about 40 µl, and preferably about 12 µl for vaping applications.

The heating element 42 is porous and permeable so as to have interconnected interstitial spaces for holding the fluid 46 in the nature of a sponge. The heating element 42 is made of an electrically conductive material having a high thermal conductivity so as to heat up upon application of electrical energy thereto. The heating element 42 may be a mesh and may be made of interwoven wire made of kanthal, nichrome, stainless steel and the like. The heating element 42 is desirably configured to have a pore size and permeability to optimize wetting of the heating element 42 with the fluid, heat transfer, and escape of volatized fluid during operation of the heater 24. The volume of the heating element 42 to be available for receiving the fluid to be vaporized may be calculated based on a given porosity and desired fluid volume. Desirably, the heating element 42 has a surface area calculated by defining the heat flux required to vaporize a desired volume of fluid in a specified time, and limiting the flux density to a desired amount, to indicate a desired thickness of the heating element 42.

An advantage of the described heater 24 is that substantially all of the fluid 46 ejected from the ejection head 22 is captured in the reservoir 40 and is in intimate contact with the interstitial spaces of the heating element 42 and heated in a manner so that the fluid 46 is vaporized.

In operation of the heater 24, the heater 24 is desirably ramped to a low preheat temperature, such as 100-150 degrees C. in advance of the fluid 46 being jetted into the reservoir 40. Then, the desired dose of the fluid 46 is jetted into the reservoir 40, and fully received by the interstitial spaces of the heating element 42. Electrical power is then applied via the electrodes 46 to the heating element 42 at a high enough power for a period of time only long enough to fully vaporize the fluid 46. The electrical power may then be immediately shut down to avoid overheating conditions.

The mass and thickness of the heating element 42 may be tuned for optimal heater warm up and vaporization efficiency based on the rate of vaporization required. The voltage/current requirements for driving the heater may likewise be tuned by adjusting the material thickness, composition and shape of the heater.

In this regard, it will be appreciated that the construction of the heater 24 enables high electrical efficiency. Because the reservoir 40 is nonconductive, no power is utilized to heat the reservoir. All of the electrical energy is used to heat the heating element 42 and to heat the fluid 46 within the heating element 42. Furthermore, the intimate contact between the heating element 42 and the fluid 46 minimizes the temperature to which the heating element 42 must be heated to vaporize the fluid 46, thus avoiding undesirable thermal degradation of the ejected fluid.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A heater for a vaporization device comprising a fluid reservoir and heating element made of an electrically conductive material selected from the group consisting of a mesh and an interwoven wire and located within the reservoir, wherein the reservoir and the heating element define a fluid volume sufficient to capture and retain a fixed volume of fluid ranging from about 10 to about 40 µl that is ejected from an ejection head associated with a fluid supply cartridge in the vaporization device, and wherein application of electrical energy to the heating element vaporizes the fixed volume of fluid in a fixed amount of time.

2. The heater of claim 1, wherein the fluid reservoir is made of a material that is not electrically conductive.

3. The heater of claim 1, wherein the fluid reservoir is made of ceramic.

4. The heater of claim 1, wherein the heating element is made of kanthal or nichrome or stainless steel or combinations thereof.

5. A vaporization device comprising a housing body, a mouthpiece attached to the housing body, and a heater disposed adjacent to the mouthpiece for vaporizing fluid ejected from an ejection head associated with a fluid supply cartridge onto the heater, wherein the heater comprises a fluid reservoir and heating element located within the reservoir and made of an electrically conductive material selected from the group consisting of a mesh and an interwoven wire, wherein the reservoir and the heating element define a fluid volume sufficient to capture and retain a fixed volume of fluid ranging from about 10 to about 40 µl that is ejected from the ejection head in the vaporization device, and wherein application of electrical energy to the heating element vaporizes the fixed volume of fluid in a fixed amount of time.

6. The vaporization device of claim 5, wherein the fluid reservoir is made of a material that is not electrically conductive.

7. The vaporization device of claim 5, wherein the fluid reservoir is made of ceramic.

8. The vaporization device of claim 5, wherein the heating element is made of kanthal or nichrome or stainless steel or combinations thereof.

9. A method for vaporizing a fluid ejected by an ejection head, comprising providing a vaporization device having an ejection head, a fluid supply cartridge associated with the ejection head, and a vaporizing heater adjacent to the ejection head;
    ejecting fluid onto the heater; and
    activating the heater during fluid ejection in order to vaporizes substantially all of the fluid ejected onto the heater,
    wherein the vaporizing heater comprises a reservoir and heating element located within the reservoir and made of an electrically conductive material selected from the group consisting of a mesh and an interwoven wire, wherein the reservoir and the heating element define a fluid volume sufficient to capture and retain a fixed volume of fluid ranging from about 10 to about 40 µl that is ejected from the ejection head in the vaporization device, and wherein application of electrical energy to the heating element vaporizes the fixed volume of fluid in a fixed amount of time.

10. The method of claim 9, wherein the fluid reservoir is made of a material that is not electrically conductive.

11. The method of claim 9, wherein the fluid reservoir is made of ceramic.

12. The method of claim 9, wherein the heating element is made of kanthal or nichrome or stainless steel or combinations thereof.

* * * * *